United States Patent
Gainor

(10) Patent No.: US 9,801,711 B2
(45) Date of Patent: *Oct. 31, 2017

(54) REINFORCED COMMISSURAL SUPPORT STRUCTURE

(71) Applicant: HLT, Inc., Maple Grove, MN (US)

(72) Inventor: John Gainor, Mendota Heights, MN (US)

(73) Assignee: HLT, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/203,396

(22) Filed: Mar. 10, 2014

(65) Prior Publication Data

US 2014/0194980 A1    Jul. 10, 2014

Related U.S. Application Data

(63) Continuation of application No. 13/208,236, filed on Aug. 11, 2011, now Pat. No. 8,696,737.

(60) Provisional application No. 61/372,803, filed on Aug. 11, 2010.

(51) Int. Cl.
*A61F 2/24* (2006.01)

(52) U.S. Cl.
CPC .......... *A61F 2/2412* (2013.01); *A61F 2/2418* (2013.01); *A61F 2/24* (2013.01)

(58) Field of Classification Search
CPC ........ A61F 2/24; A61F 2/2409; A61F 2/2412; A61F 2/2418
See application file for complete search history.

(56) References Cited

U.S. PATENT DOCUMENTS

| 5,549,665 | A | 8/1996 | Vesely et al. |
| 6,016,810 | A | 1/2000 | Ravenscroft |
| 6,126,686 | A | 10/2000 | Badylak et al. |

(Continued)

FOREIGN PATENT DOCUMENTS

| DE | 102005052628 A1 | 5/2007 |
| JP | 2002537943 A | 11/2002 |

(Continued)

OTHER PUBLICATIONS

United States Patent and Trademark Office, Office Action mailed Feb. 27, 2014 in U.S. Appl. No. 13/651,249, 11 pages.

(Continued)

*Primary Examiner* — David Isabella
*Assistant Examiner* — Dinah Baria
(74) *Attorney, Agent, or Firm* — Inskeep IP Group, Inc.

(57) ABSTRACT

A device and method for controlling commissural tip deflection of a prosthetic valve, thereby both preventing failure due to repeated movement and/or uneven loading of the commissural points and also improving coaptation of the valve leaflets, including connecting reinforcing material between the commissural points so a spring-like span is created across the points. The spanning material may be in the form of a ring that is lashed, sewn or otherwise connected to the commissural points. The reinforcing material may form curved segments between the commissural points that extend outwardly to form sinuses behind the leaflets of the prosthetic valve. The reinforcing material may also extend in an upstream direction to avoid interfering with blood flowing out of the prosthetic valve.

20 Claims, 3 Drawing Sheets

(56) References Cited

U.S. PATENT DOCUMENTS

| | | | |
|---|---|---|---|
| 6,168,614 | B1 | 1/2001 | Andersen et al. |
| 6,524,339 | B1 | 2/2003 | Adams |
| 6,592,614 | B2 | 7/2003 | Lenker et al. |
| 6,719,781 | B1 | 4/2004 | Kim |
| 7,001,425 | B2 | 2/2006 | McCullagh et al. |
| 7,252,681 | B2 | 8/2007 | Berg et al. |
| 7,329,279 | B2 | 2/2008 | Haug et al. |
| 2002/0032481 | A1 | 3/2002 | Gabbay |
| 2002/0133226 | A1* | 9/2002 | Marquez ............... A61F 2/2412 623/2.11 |
| 2004/0073293 | A1 | 4/2004 | Thompson |
| 2004/0220664 | A1 | 11/2004 | Chobotov |
| 2004/0260333 | A1 | 12/2004 | Dubrul et al. |
| 2005/0075720 | A1 | 4/2005 | Nguyen et al. |
| 2005/0137702 | A1 | 6/2005 | Haug et al. |
| 2005/0222674 | A1 | 10/2005 | Paine |
| 2005/0283231 | A1 | 12/2005 | Haug et al. |
| 2006/0271166 | A1 | 11/2006 | Thill et al. |
| 2007/0142906 | A1 | 6/2007 | Figulla et al. |
| 2008/0071362 | A1 | 3/2008 | Tuval et al. |
| 2009/0076598 | A1 | 3/2009 | Salahieh et al. |
| 2009/0222076 | A1 | 9/2009 | Figulla et al. |
| 2010/0168839 | A1 | 7/2010 | Braido et al. |
| 2011/0218619 | A1* | 9/2011 | Benichou et al. ........... 623/2.11 |
| 2011/0264206 | A1 | 10/2011 | Tabor |
| 2012/0209370 | A1 | 8/2012 | Thill et al. |
| 2013/0144383 | A1 | 6/2013 | Thill et al. |

FOREIGN PATENT DOCUMENTS

| | | |
|---|---|---|
| JP | 2003506133 A | 2/2003 |
| JP | 2004503327 A1 | 2/2004 |
| JP | 2012-223618 A | 11/2012 |
| WO | WO0053130 A1 | 9/2000 |
| WO | WO01/10316 A1 | 2/2001 |
| WO | WO02/05729 A2 | 1/2002 |

OTHER PUBLICATIONS

Japanese Patent Office, Office Action dated Jul. 25, 2103 in Japanese Patent Application No. 2012-108576, 1 page.
United States Patent and Trademark Office, Office Action mailed Jun. 12, 2013 in U.S. Appl. No. 13/458,023, 8 pages.
European Patent Office, Examination Report dated Feb. 14, 2013 in European Patent Application No. 06771666, 3 pages.
Japanese Patent Office, Office Action dated Jan. 28, 2013 with English translation in Japanese Patent Application No. 2008-513838, 11 pages.
State Intellectual Property Office, P.R. China, Notification to Go Through Formalities of Registration mailed Jan. 4, 2013 in Chinese Patent Application No. 201010533068-8 with English translation, 5 pages.
Canadian Intellectual Property Office, Examiner's Report dated Dec. 6, 2012 in Canadian Patent Application No. 2,613,958, 3 pages.
United States Patent and Trademark Office, Office Action mailed Nov. 14, 2012 in U.S. Appl. No. 11/443,814, 11 pages.
United States Patent and Trademark Office, Office Action mailed Nov. 13, 2012 in U.S. Appl. No. 13/458,023, 11 pages.
IP Australia, Examination Report dated Jul. 16, 2012 in Australian Patent Application No. 2011265440, 3 pages.
State Intellectual Property Office, P.R. China, Office Action mailed Jun. 1, 2012 with English translation in Chinese Patent Application No. 20100533068-8, 4 pages.
Japanese Patent Office, Final Office Action dated May 2, 2012 with English translation in Japanese Patent Application No. 2008-513838 with English translation, 4 pages.
Japan Patent Office, Official Action dated Sep. 28, 2011 in Japanese Patent Application No. 2008-513838 with English translation, 7 pages.
IP Australia, Notice of Acceptance mailed Sep. 15, 2011 in Australian Patent Application No. 2006251938, 3 pages.
State Intellectual Property Office, P.R. China, Office Action mailed Jul. 29, 2011 with English translation in Chinese Patent Application No. 201010533068-8, 4 pages.
IP Australia, Examination Report dated Apr. 18, 2011 in Australian Patent Application No. 2006251938, 2 pages.
United States Patent and Trademark Office, Final Office Action mailed Dec. 14, 2010 in U.S. Appl. No. 11/443,814, 10 pages.
State Intellectual Property Office, P.R. China, Notification to Go Through Formalities of Registration mailed Aug. 3, 2010 in Chinese Patent Application No. 200680027512 with English translation, 5 pages.
United States Patent and Trademark Office, Final Office Action mailed Jul. 22, 2010 in U.S. Appl. No. 11/443,814, 9 pages.
United States Patent and Trademark Office, Office Action mailed Dec. 29, 2009 in U.S. Appl. No. 11/443,814, 7 pages.
State Intellectual Property Office, P.R. China, Office Action mailed Nov. 27, 2009 with English translation in Chinese Patent Application No. 200680027512-0, 6 pages.
United States Patent and Trademark Office, Office Action mailed Apr. 17, 2009 in U.S. Appl. No. 11/443,814, 7 pages.
United States Patent and Trademark Office, Final Office Action mailed Nov. 17, 2008 in U.S. Appl. No. 11/443,814, 10 pages.
United States Patent and Trademark Office, Office Action mailed Mar. 18, 2008 in U.S. Appl. No. 11/443,814, 10 pages.
WIPO, U.S. International Preliminary Examining Authority, International Preliminary Report on Patentability mailed Nov. 30, 2007 in International Patent Application No. PCT/US2006/021021, 7 pages.
WIPO, U.S. International Search Authority, International Search Report and Written Opinion mailed Sep. 5, 2007 in International Patent Application No. PCT/US2006/021021, 10 pages.
United States Patent and Trademark Office, Notice of Allowance mailed Dec. 13, 2013 in U.S. Appl. No. 13/208,236, 7 pages.
United States Patent and Trademark Office, Final Office Action mailed Aug. 23, 2013 in U.S. Appl. No. 13/208,236, 12 pages.
United States Patent and Trademark Office, Office Action mailed Mar. 14 in U.S. Appl. No. 13/208,236, 13 pages.

* cited by examiner

REINFORCED COMMISSURAL SUPPORT STRUCTURE

RELATED APPLICATIONS

This application is a continuation of U.S. patent application Ser. No. 13/208,236 filed Aug. 11, 2011 entitled claims priority to U.S. Provisional Patent Application Ser. No. 61/372,803 filed Aug. 11, 2010 entitled Reinforced Commissural Support Structure Reinforced Commissural Support to Gainor, the entirety of which is incorporated by reference herein. This application also incorporates by reference U.S. patent application Ser. No. 11/443,814 filed May 30, 2006 entitled Stentless Support Structure to Thill et al.

BACKGROUND OF THE INVENTION

There has been a significant movement toward developing and performing cardiovascular surgeries using a percutaneous approach. As used herein, the term "percutaneous" is defined as an alternative to a surgical approach whereby one or more catheters are introduced into the body via a small puncture, and typically into a body lumen, for example, the femoral artery. Through the one or more catheters, tools and devices can be delivered to a desired area, such as in the cardiovascular system, to perform any number of complicated procedures that normally otherwise require an invasive surgical procedure. Such approaches greatly reduce the trauma endured by the patient and can significantly reduce recovery periods. The percutaneous approach is particularly attractive as an alternative to performing open-heart surgery.

Valve replacement surgery provides one example of an area where percutaneous solutions are being developed. A number of diseases result in a thickening, and subsequent immobility or reduced mobility, of heart valve leaflets. Such immobility also may lead to a narrowing, or stenosis, of the passageway through the valve. The increased resistance to blood flow that a stenosed valve presents can eventually lead to heart failure and ultimately death.

Treating valve stenosis or regurgitation has historically involved complete removal of the existing native valve through an open-heart procedure followed by the implantation of a prosthetic valve. Naturally, this is a heavily invasive procedure and inflicts great trauma on the body leading usually to great discomfort and considerable recovery time. It is also a sophisticated procedure that requires great expertise and talent to perform.

Recently, however, much attention has been given to the development of replacement heart valves that can be delivered percutaneously through a catheter. Understandably, size is a key design consideration when developing a device that is catheter-deliverable. The device must either be smaller than the lumen of a catheter, or able to be compressed until it is. In the case of a prosthetic valve, the size of the valve is determined by the native valve being replaced, or at least by the vasculature into which the percutaneous valve is being placed. A valve that is too small will likely fail to meet the demand for blood through the vessel and act as a source for future stenosis. The catheter delivering the valve will necessarily have to be smaller than the targeted blood vessel. As such, percutaneously-delivered heart valves must be capable of being compressed and loaded into a catheter, and subsequently expanded upon delivery.

Percutaneously-delivered heart valves must also, and arguably most importantly, be able to withstand the rigors of being repetitively opened and closed during use. Considering a heart, beating at an average of 70 beats per minute, beats over 100,000 times a day, any flaw in a prosthetic valve, whether it be a design flaw or a mechanical flaw, will greatly reduce the lifespan of the valve and potentially its user.

Hence, designing a valve that is both rugged enough for long-term use, and compressible enough to be placed into a catheter, is a daunting task. One promising design is shown and described in U.S. patent application Ser. No. 11/443,814, entitled Stentless Support Structure by Thill et al. and is incorporated by reference herein in its entirety. In short, the embodiments shown in this application include a support structure 5 (see, e.g. FIG. 1) and a valve 10. The support structure 5 is preferably a braided tube made out of Nitinol or a similar material. The braided tube folds in on itself one or more times upon deployment to multiply its radial strength.

The valve 10 is constructed to mimic a native valve and generally comprises one or more sheets of porcine tissue 12 attached to a commissural wireform 14. The wireform 14 gives the tissue 12 the correct shape in order to form leaflets that coapt during diastole and separate during systole. The tissue 12 is carefully sewn or otherwise attached to the support wire 14 such that, over time, the tissue does not tear or separate from the wireform 14. As such the wireform 14 flexes back and forth as the valve tissue 12 opens and closes.

Movement of the wireform 14 during cardiac function will cause the materials of a prosthetic valve to fatigue. The components of the prosthetic device should be able to withstand the expected loads and material cycles to which it will be subjected in the human cardiovascular system. Because the integrity of the wireform 14 affects the appropriate function of the valve 10, it would thus be desirable to modify the wireform 14 in order to improve the performance of the valve 10.

BRIEF SUMMARY OF THE INVENTION

The invention provides a solution to the aforementioned need to increase the lifespan of a prosthetic valve. The invention provides a device that reinforces the commissural points of a wireform without interfering with the function of the valve. The device of the invention is useable with a wide variety of valve designs, regardless of the stent or support structure that anchors the device to the vessel.

More specifically, the invention provides the wireform with a secondary, reinforcing component that acts as a compression spring between each of the commissural points of a prosthetic valve. Advantageously, the invention does not eliminate tip deflection of the commissural points, but controls the deflection to a known level at a given valve closing pressure. As such, the deflection of the wireform and the material strain under known hydraulic valve pressures can be tuned such that the wire fatigue limit will not be reached and the wireform will survive the requirements of both testing and real-world use in a patient.

DETAILED DESCRIPTION OF THE INVENTION

Figure 1:
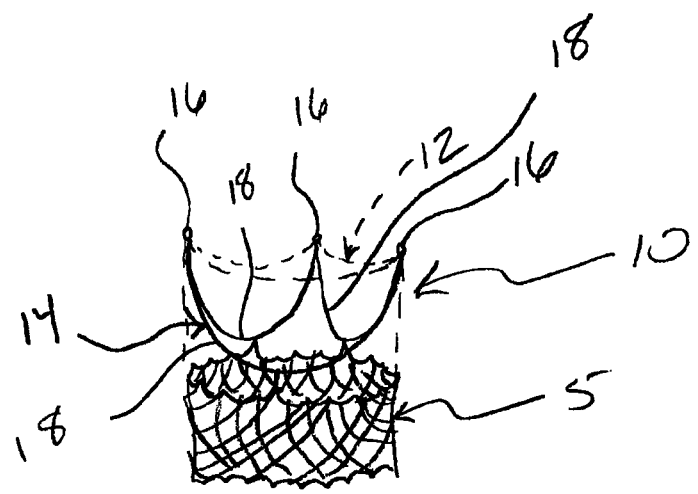
FIG. 1 is a perspective view of an example of a prior art valve design.

Referring now to the Figures and first to FIG. 1, there is shown a prior art prosthetic valve design that generally includes a support structure 5 and a valve 10. The support structure 5 is typically a stent or a mesh, braided tube made out of a material such as Nitinol.

The valve 10 is constructed to mimic a native valve and generally comprises one or more sheets of porcine tissue 12 attached to a commissural wireform 14. The wireform 14 gives the tissue 12 the correct shape in order to form leaflets that coapt during diastole and separate during systole. The wireform 14 forms commissural points 16 separated by arcuate portions 18. The arcuate portions 18 are attached to the support structure 5. The commissural points 16 facilitate natural and efficient opening and closing of the valve 10.

The tissue 12 of the valve 10 is carefully sewn or otherwise attached to the wireform 14 such that, over time, the tissue does not tear or separate from the wireform 14. The tissue is shown in phantom line in order to show the detail of the wireform 14, which is a relevant component of the prior art valve to the invention. The components of FIG. 1 are not shown in FIGS. 2, 3 and 4 for purposes of clarity. Additionally, the device of the invention could be used with other prosthetic valve designs that utilize commissural points.

Figure 2:
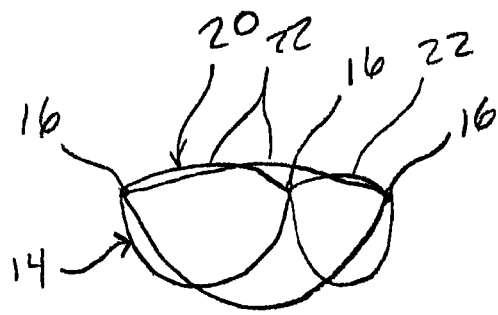
FIG. 2 is a perspective view of an embodiment of the invention.

Referring now to FIG. 2, there is shown a device 20 of the invention. The device 20 generally comprises a reinforcing ring that spans and connects adjacent commissural points 16 of a wireform 14. The device 20 may include separate members (three for a tricuspid valve design such as that shown in the figures) spanning each of the adjacent pairs of commissural points 16. Preferably, however, the device 20 comprises a ring formed from a single wire of an appropriate biocompatible material, such as Nitinol, stainless steel, or the like. Additionally, the device 20 may be created from a wire, or may be laser-cut from a tube, to create a seamless loop.

The device 20 may be connected to the wireform 14 in a variety of ways. Positive results have been achieved by lashing the device 20 to the commissural points of the wireform 14, which may be constructed with loops (see FIG. 1) for receiving lashing material. Alternatively, the connection method could be a snap rivet or other mechanical connector locking the device 20 to the commissural points 16 of the wireform 14, or the device 20 and the wireform 14 could be welded, bonded, brazed or otherwise joined at the commissural points 16.

The shape of the device 20 of the invention is designed to achieve multiple objectives. First, the device 20 adds rigidity to the wireform 14 to limit the deflection of the commissural points 16 in order to reduce the stress on the wireform caused by wireform tip deflection. Second, while limiting the deflection, the device 20 is not entirely rigid and does allow a degree of flexibility in order to reduce the stress on the tissue 12 and the tissue connection component. Finally, as the device 20 is intended to limit deflection of the commissural points 16, it also acts to normalize the movements of the tissue cusps 12, preventing asymmetric cusp motion and thus the elevated stresses that arise from cusp asymmetry during valve function.

The embodiment shown in FIG. 2 accomplishes this by providing curved sections 22 between each of the commissural points 16. The curved sections 22 in this embodiment extend generally upward (or downstream) of the valve 10.

Figure 3:
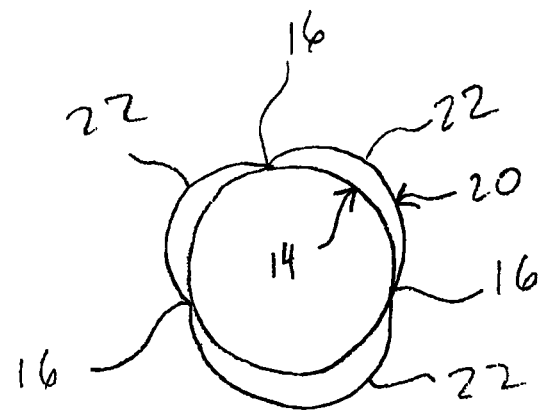
FIG. 3 is a top plan view of an embodiment of the invention.

Alternatively, as shown in the embodiment of FIG. 3, the curved sections 22 could extend generally outwardly. In this embodiment, the device 20 not only reinforces the commissural points 16, it also places gentle outward pressure on the vessel walls. Doing so creates sinuses behind the tissue 12 of the valve 10 to enhance coaptation during diastole. The outward curved sections 22 of this embodiment also assist in anchoring the valve 10 as slight migration into the vessel walls may occur, depending on the size of the device 20 in relation to the size of the vascular implantation site. The curved sections 22 of this embodiment may be level with the commissural points 16 or may extend slightly upward (downstream) as well such that the curved sections 22 are angled both upward and outward.

Figure 4:
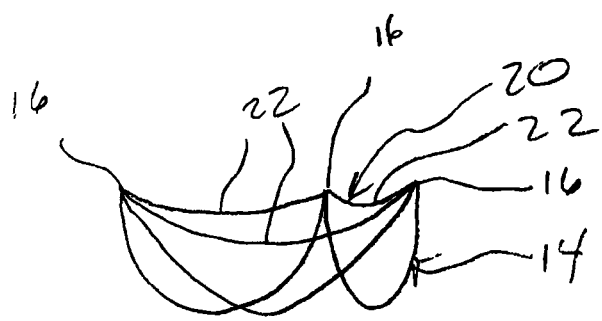
FIG. 4 is a perspective view of an embodiment of the invention.

In one embodiment, shown in FIG. 4, the curved sections 22 extend downwardly, in an upstream direction. This design is particularly advantageous in situations as space at the target implantation site may be longitudinally limited. Additionally, the curved sections 22 may extend outwardly, like those of FIG. 3, in order to extend into the natural sinus spaces, or to create or supplement sinus space behind the valve leaflets in order to assist in coaptation during diastole.

Figure 5:
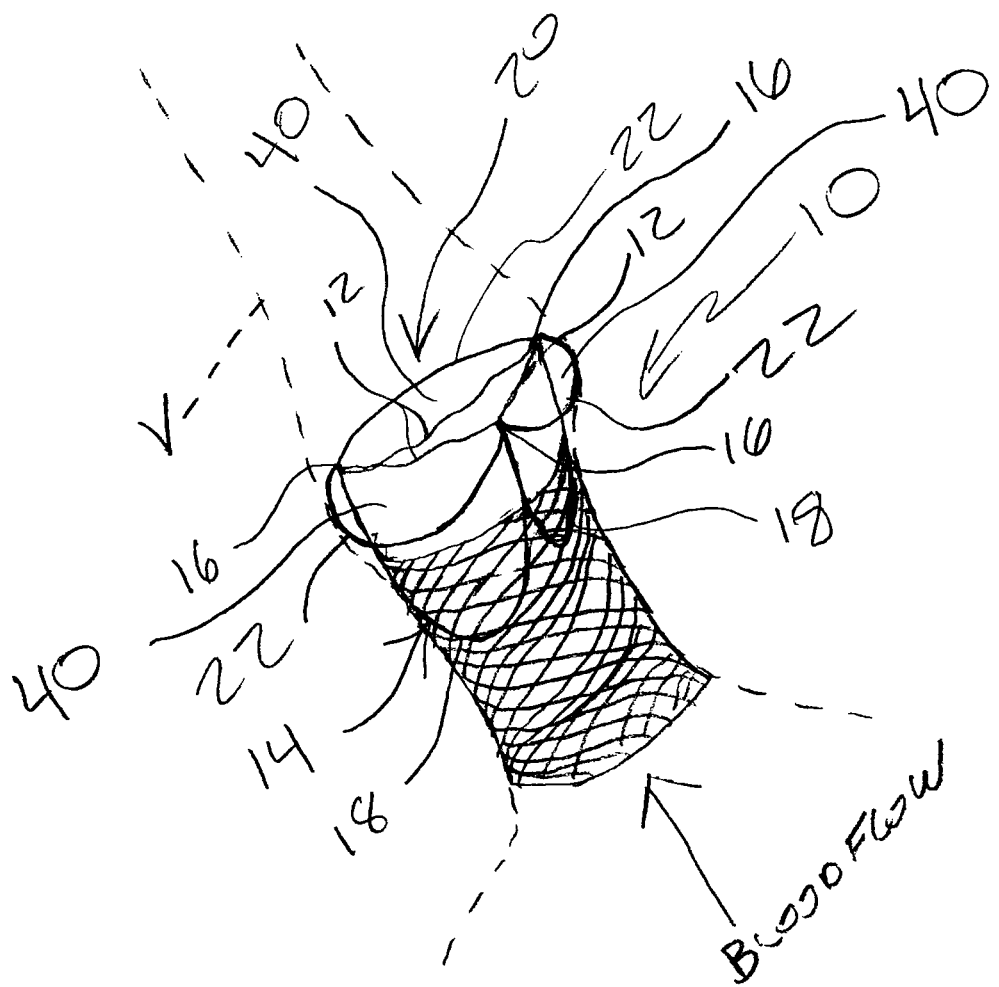
FIG. 5 is a perspective view of an embodiment of the invention.

FIG. 5 shows a device 20 of the invention implanted in a vessel V, shown in phantom lines. Also shown in this figure are the remaining components of the prosthetic valve 10, namely, the flexible material 12 that forms the leaflets, typically porcine tissue or other biocompatible material, the wireform 14 forming the commissural points 16, which are separated by arcuate portions 18. The curved sections 22 of the device 20 are shown as extending outwardly and slightly downwardly (upstream). The walls of the vessel V are thus pushed outwardly slightly and sinuses 40 are formed behind the leaflets. Advantageously, no material from the device 20 extends into the flow path exiting the valve 10.

In each of the aforementioned embodiments, the bowing of the device 20 between each of the commissural points 16 acts as a compression spring. The geometry of this compression spring may be modulated to control the wireform tip deflection to the extent desired based on the forces that the device is expected to withstand in the cardiovascular system.

Additionally, the sections 22 of the device 20 may be constructed such that the device 20 can be used in conjunction with a delivery system to provide a single-point retention system useful for implantation of the device using a low-profile catheter. In this manner, the sections 22 of device 20 may be constructed such that in a preliminary deployed configuration, the sections 22 are all drawn to the center of the wireform 14. In the secondary deployed configuration, these sections 22 are allowed to move to their functional position between each of the commissural points 16 as a precursor to device release or upon release of the device itself.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A prosthetic valve assembly comprising:
a support structure having an upstream portion and a downstream portion;
a wireform having commissural points separated by arcuate portions, said arcuate portions connected to said downstream portion of said support structure such that said commissural points are downstream of a downstream end of said support structure; said wireform defining a central longitudinal axis;
flexible material connected to said wireform to form valve leaflets between said commissural points;
reinforcement material downstream of an upstream end of said arcuate portions and extending from and spanning between said commissural points, said reinforcement material controlling flexure of said commissural points;
wherein said reinforcement material spanning said commissural points extends radially outwardly of said longitudinal axis.

2. The prosthetic valve of claim 1 wherein said support structure comprises a Nitinol braid.

3. The prosthetic valve of claim 2 wherein said flexible material comprises tissue.

4. The prosthetic valve of claim 3 wherein said tissue comprises biological tissue.

5. The prosthetic valve of claim 4 wherein said biological tissue comprises porcine tissue.

6. The prosthetic valve of claim 1 wherein said reinforcement material comprises a reinforcement ring that connects each of said commissural points.

7. The prosthetic valve of claim 6 wherein said reinforcement ring comprises a single wire ring.

8. The prosthetic valve of claim 6 wherein said reinforcement ring comprises a seamless loop cut from a tube.

9. The prosthetic valve of claim 1 wherein said reinforcement material comprises Nitinol.

10. The prosthetic valve of claim 1 wherein said reinforcement material spanning said commissural points defines sinus space outside of said flexible material.

11. The prosthetic valve of claim 1 wherein said reinforcement material spanning said commissural points does not extend downstream of said commissural points.

12. A method of controlling flexure of a wireform for a prosthetic valve having a support structure and a wireform forming commissural points separated by arcuate portions said arcuate portions connected to a downstream portion of the support structure, comprising connecting said commissural points together with reinforcement material located downstream of an upstream end of said arcuate portions said reinforcement material extending radially outwardly of a longitudinal axis of said wireform.

13. The method of claim 12 wherein connecting said commissural points together with reinforcement material comprises connecting a reinforcement ring to said commissural points.

14. The method of claim 12 wherein connecting said commissural points together with reinforcement material comprises connecting said commissural points with Nitinol reinforcements.

15. The method of claim 12 wherein connecting said commissural points together with reinforcement material comprises lashing said reinforcement material to each of said commissural points.

16. The method of claim 12 wherein connecting said commissural points together with reinforcement material comprises defining sinus spaces radially outward of leaflets of said prosthetic valve.

17. A method of controlling inward flexure of commissural tip deflection of a prosthetic valve assembly including a wireform having arcuate portions attached to a downstream portion of a support structure comprising extending reinforcement material from commissural points of a wireform such that said reinforcement material extends directly radially outward from a longitudinal axis of said prosthetic valve assembly and said reinforcement material is located downstream of an upstream portion of said wireform.

18. The method of claim 17 wherein extending reinforcement material from commissural points of a wireform comprises connecting a reinforcement ring to said commissural points.

19. The method of claim 17 wherein extending reinforcement material from commissural points of a wireform defines sinus spaces radially outward of leaflets of said prosthetic valve.

20. The method of claim 17 wherein extending reinforcement material from commissural points of a wireform comprises lashing said reinforcement material to each of said commissural points.

* * * * *